United States Patent
Feng et al.

(10) Patent No.: US 9,248,281 B2
(45) Date of Patent: Feb. 2, 2016

(54) PACEMAKERS AND PACEMAKER LEADS

(75) Inventors: Chen Feng, Beijing (CN); Li Qian, Beijing (CN); Li Fan, Beijing (CN); Wen-Mei Zhao, Beijing (CN); Liang Liu, Beijing (CN); Yu-Quan Wang, Beijing (CN)

(73) Assignees: Tsinghua University, Beijing (CN); HON HAI PRECISION INDUSTRY CO., LTD., New Taipei (TW)

( * ) Notice: Subject to any disclaimer, the term of this patent is extended or adjusted under 35 U.S.C. 154(b) by 351 days.

(21) Appl. No.: 13/527,801

(22) Filed: Jun. 20, 2012

(65) Prior Publication Data

US 2013/0110213 A1  May 2, 2013

(30) Foreign Application Priority Data

Oct. 28, 2011 (CN) .......................... 2011 1 0333502

(51) Int. Cl.
*A61N 1/05* (2006.01)
*A61N 5/10* (2006.01)
*A61N 1/08* (2006.01)
*B82Y 5/00* (2011.01)
*B82Y 30/00* (2011.01)

(52) U.S. Cl.
CPC ........ *A61N 1/056* (2013.01); *A61N 1/05* (2013.01); *A61N 5/1001* (2013.01); *A61N 2001/086* (2013.01); *B82Y 5/00* (2013.01); *B82Y 30/00* (2013.01)

(58) Field of Classification Search
CPC ... A61N 1/05; A61N 1/056; A61N 2001/086; B82Y 5/00; B82Y 30/00
USPC ........................ 600/373; 607/5, 119
See application file for complete search history.

(56) References Cited

U.S. PATENT DOCUMENTS

| | | | |
|---|---|---|---|
| 5,713,945 A * | 2/1998 | Fischer et al. ............... 607/122 |
| 6,295,476 B1 * | 9/2001 | Schaenzer .................. 607/122 |
| 7,493,160 B2 | 2/2009 | Weber et al. |
| 7,512,447 B2 | 3/2009 | Marshall et al. |
| 7,596,415 B2 | 9/2009 | Brabec et al. |
| 8,048,256 B2 | 11/2011 | Feng et al. |
| 2002/0077520 A1 * | 6/2002 | Segal et al. .................. 600/1 |
| 2004/0051432 A1 | 3/2004 | Jiang et al. |
| 2006/0272701 A1 * | 12/2006 | Ajayan et al. ............... 136/263 |
| 2009/0062895 A1 | 3/2009 | Stahmann et al. |
| 2009/0194313 A1 | 8/2009 | Jiang et al. |
| 2009/0255706 A1 | 10/2009 | Jiang et al. |
| 2010/0147829 A1 * | 6/2010 | Liu et al. .................... 219/546 |
| 2011/0026758 A1 | 2/2011 | Wang et al. |
| 2011/0160829 A1 | 6/2011 | Foster et al. |

(Continued)

FOREIGN PATENT DOCUMENTS

| CN | 1460638 | 12/2003 |
| CN | 1484275 | 3/2004 |

(Continued)

*Primary Examiner* — William Levicky
(74) *Attorney, Agent, or Firm* — Novak Druce Connolly Bove + Quigg LLP (57) ABSTRACT

A pacemaker is provided. The pacemaker includes a pulse generator and an electrode line connecting with the pulse generator. The electrode line includes a conductor, an insulation layer and a shielding layer. The insulation layer is located on an outer surface of the conductor. The shielding layer is located on an outer surface of the first insulation layer. The shielding layer is a carbon nanotube structure having a plurality of radioactive particles therein.

15 Claims, 10 Drawing Sheets

(56) References Cited

U.S. PATENT DOCUMENTS

| | | | |
|---|---|---|---|
| 2011/0301657 A1* | 12/2011 | Walsh et al. | ............ 607/5 |
| 2012/0053649 A1 | 3/2012 | Liu et al. | |
| 2012/0271394 A1 | 10/2012 | Foster et al. | |

FOREIGN PATENT DOCUMENTS

| | | |
|---|---|---|
| CN | 1943805 | 4/2007 |
| CN | 101499331 | 8/2009 |
| CN | 101757723 | 6/2010 |
| CN | 101925379 | 12/2010 |
| CN | 101927057 | 12/2010 |
| CN | 101990147 | 3/2011 |
| TW | 200945372 | 11/2009 |
| TW | 201039670 | 11/2010 |
| TW | I345792 | 7/2011 |

* cited by examiner

PACEMAKERS AND PACEMAKER LEADS

RELATED APPLICATIONS

This application claims all benefits accruing under 35 U.S.C. §119 from China Patent Application No. 201110333502.2, filed on Oct. 28, 2011 in the China Intellectual Property Office, the disclosure of which is incorporated herein by reference. This application is related to common-assigned applications entitled, "ELECTRODE LEAD OF PACEMAKER AND PACEMAKER USING THE SAME," Ser. No. 13/527,820, filed on Jun. 20, 2012, US Patent Application Publication No. 2013/0110215; "METHOD FOR MAKING PACEMAKER ELECTRODE LEAD," Ser. No. 13/527,780, filed on Jun. 20, 2012, US Patent Application Publication No. 2013/0104396; "ELECTRODE LEAD OF PACEMAKER AND PACEMAKER USING THE SAME," Ser. No. 13/527,782, filed on Jun. 20, 2012, U.S. Pat. No. 8,825,178; "ELECTRODE LEAD OF PACEMAKER AND PACEMAKER," Ser. No. 13/527,784, filed on Jun. 20, 2012, US Patent Application Publication No. 2013/0109986; "PACEMAKERS AND PACEMAKER LEADS," Ser. No. 13/527,792, filed on Jun. 20, 2012, US Patent Application Publication No. 20130109905; "ELECTRODE LEAD OF PACEMAKER AND PACEMAKER USING THE SAME," Ser. No. 13/527,808, filed on Jun. 20, 2012, US Patent Application Publication No. 20130110214; "ELECTRODE LEAD AND PACEMAKER USING THE SAME," Ser. No. 13/527,836, filed on Jun. 20, 2012; and "ELECTRODE LEAD AND PACEMAKER USING THE SAME," Ser. No. 13/527,849, filed on Jun. 20, 2012, U.S. Pat. No. 8,583,259.

BACKGROUND

1. Technical Field

The present application is related to pacemakers and pacemaker leads, and more particularly to pacemakers and pacemaker leads using carbon nanotubes.

2. Description of Related Art

Pacemakers are a kind of electrical therapy apparatuses which can be implanted into an organ or a tissue of human beings to treat the organ or the tissue of human beings. The pacemaker generally includes a power, a pulse generator and an electrode line. An electrical pulse signal can be generated by the pulse generator and transported to an organ or a tissue by the electrode line for stimulating the organ or the tissue. Thus, dysfunctions of the organ or the tissue of human beings can be treated.

However, when the pacemaker is implanted into the organ or the tissue of human, an excessive fibrotic tissue growth can take place on the electrode line, thus making the electrode line difficult to be removed from the organ or the tissue of human beings after therapy. Additionally, a conductor in the electrode line is made of metal or alloy and the conductor has small diameter, so a mechanical strength of the electrode line is low.

What is needed, therefore, is to provide a pacemaker and a pacemaker lead, which can overcome the above-described shortcomings.

BRIEF DESCRIPTION OF THE DRAWINGS

Many aspects of the embodiments can be better understood with reference to the following drawings. The components in the drawings are not necessarily to scale, the emphasis instead being placed upon clearly illustrating the principles of the present disclosure. Moreover, in the drawings, like reference numerals designate corresponding parts throughout the several views.

DETAILED DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Figure 1:
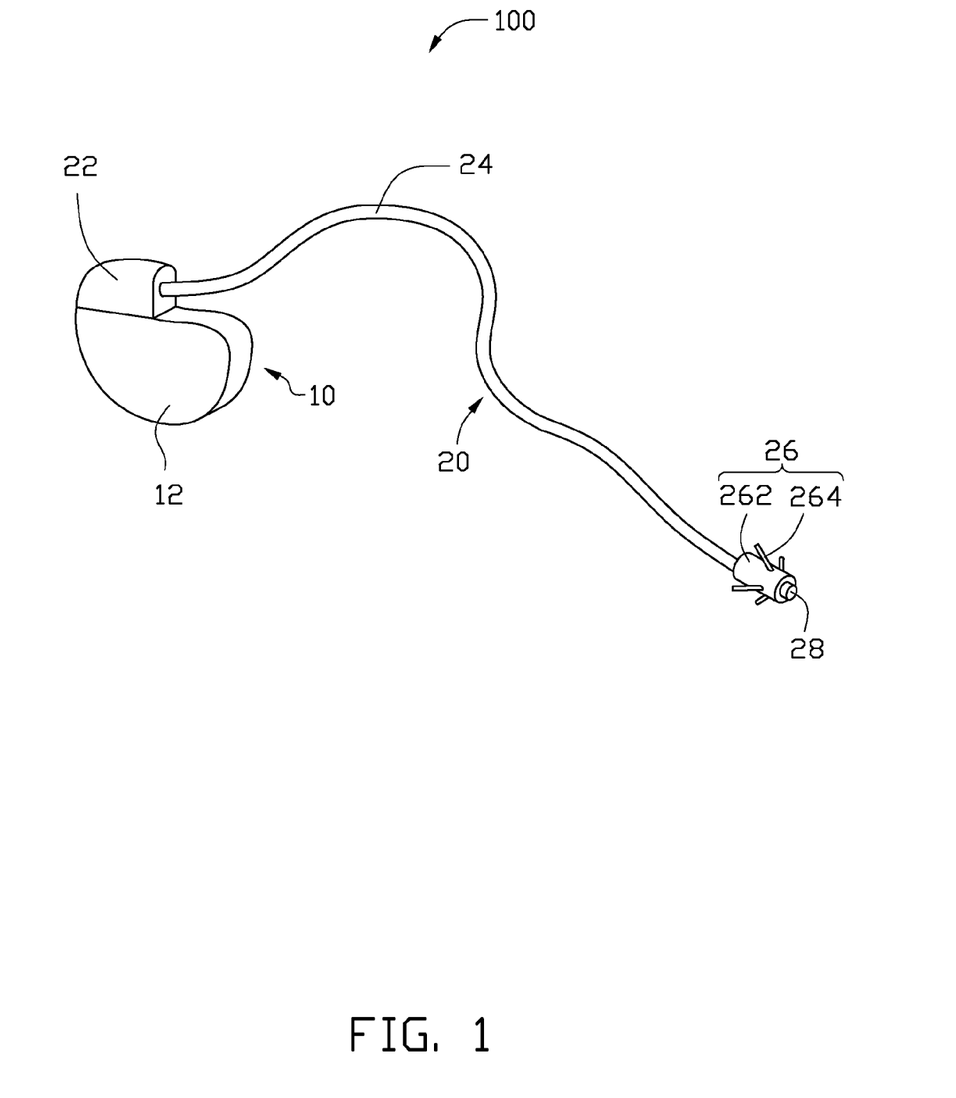
FIG. 1 shows a schematic structural view of one embodiment of a pacemaker.

Referring to FIG. 1, a pacemaker 100 of one embodiment is provided. The pacemaker 100 can be a brain pacemaker or a cardiac pacemaker. The pacemaker 100 is a unipolar pacemaker. The pacemaker 100 includes a pulse generator 10 and an electrode line 20 electrically connected to the pulse generator 10. The pulse generator 10 can generate electrical pulse signals traveling through the electrode line 20 to stimulate the brain tissue or the heart tissue.

The pulse generator 10 includes a shell 12, a power source (not show) and a control circuit (not show). The power source and the control circuit are packaged in the shell 12. The power source powers the control circuit. The power source can be a lithium battery or a fuel cell. In one embodiment, the power source is a lithium/iodine cell. The control circuit can generate the electrical pulse signals. In one embodiment, the electrical pulse signals are rectangular pulses having a pulse width in a range from about 0.5 ms to about 0.6 ms. The shell 12 can be made of metals or alloys having bio-compatibility and corrosion resistance characteristics to protect internal components. In one embodiment, the shell 12 is made of titanium.

The electrode line 20 includes an interface 22, a lead 24, a fixing member 26 and an electrode 28. The interface 22 and the electrode 28 are located at different ends of the lead 24. The fixing member 26 is fixed to a periphery of the lead 24 near the electrode 28. The fixing member 26 can be inserted into a human body to fix the lead 24. The interface 22 includes at least one conductive contact (not show). The electrode 28 can be electrical connected to the control circuit through the lead 24 and the at least one conductive contact of the interface 22.

Figure 2:
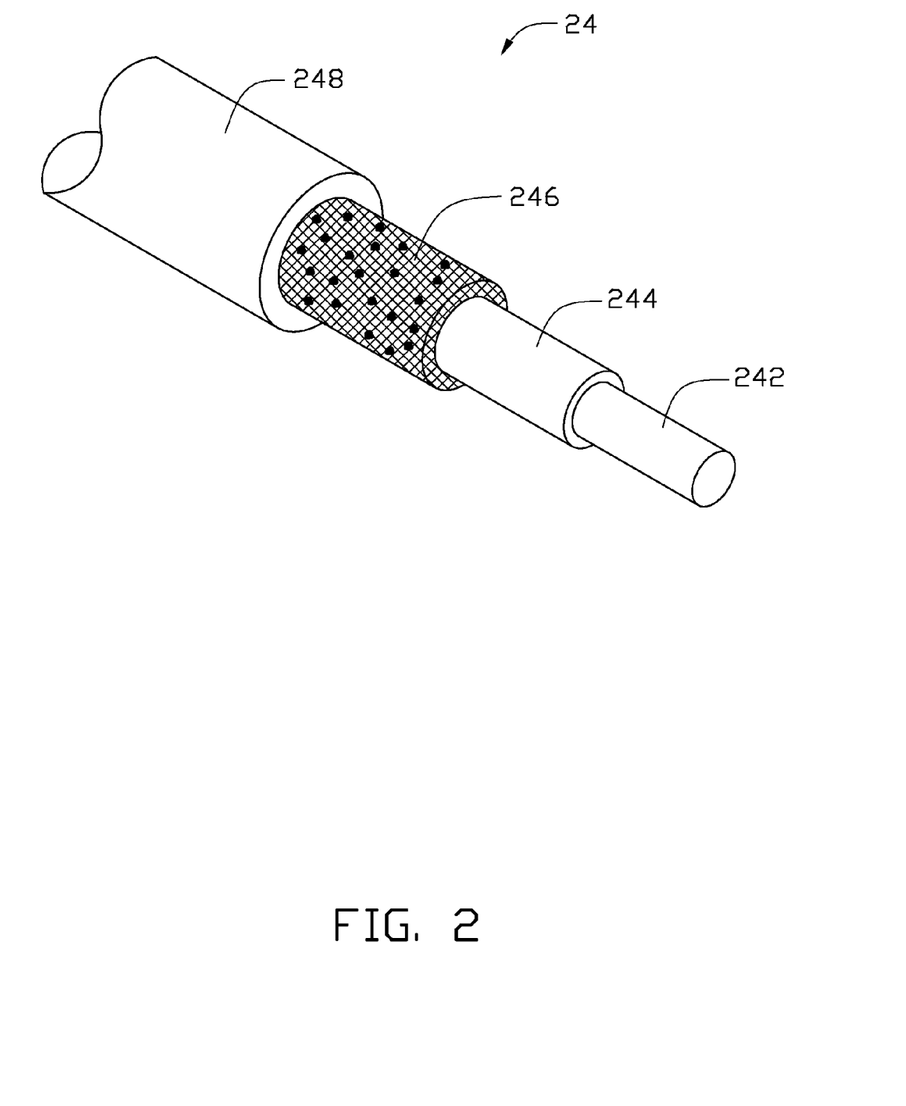
FIG. 2 shows a schematic structural view of a lead of the pacemaker of FIG. 1.

Referring to FIG. 2, the lead 24 includes a first conductor 242, an insulation layer 244, a shielding layer 246, and a sheath 248 arranged from inside to outside. The insulation layer 244 is located between the first conductor 242 and the shielding layer 246 to make the first conductor 242 and the shielding layer 246 insulate from each other. The sheath 248 is located on an outer surface of the shielding layer 246 to protect the lead 24.

A first end of the first conductor 242 is electrically connected to the at least one conductive contact of the interface 22. A second end of the first conductor 242 is electrically connected to the electrode 28. Thus, the electrical pulse signals generated from the control circuit can be transmitted to the electrode 28 through the first conductor 242. The first conductor 242 can be a carbon nanotube wire.

Figure 3:
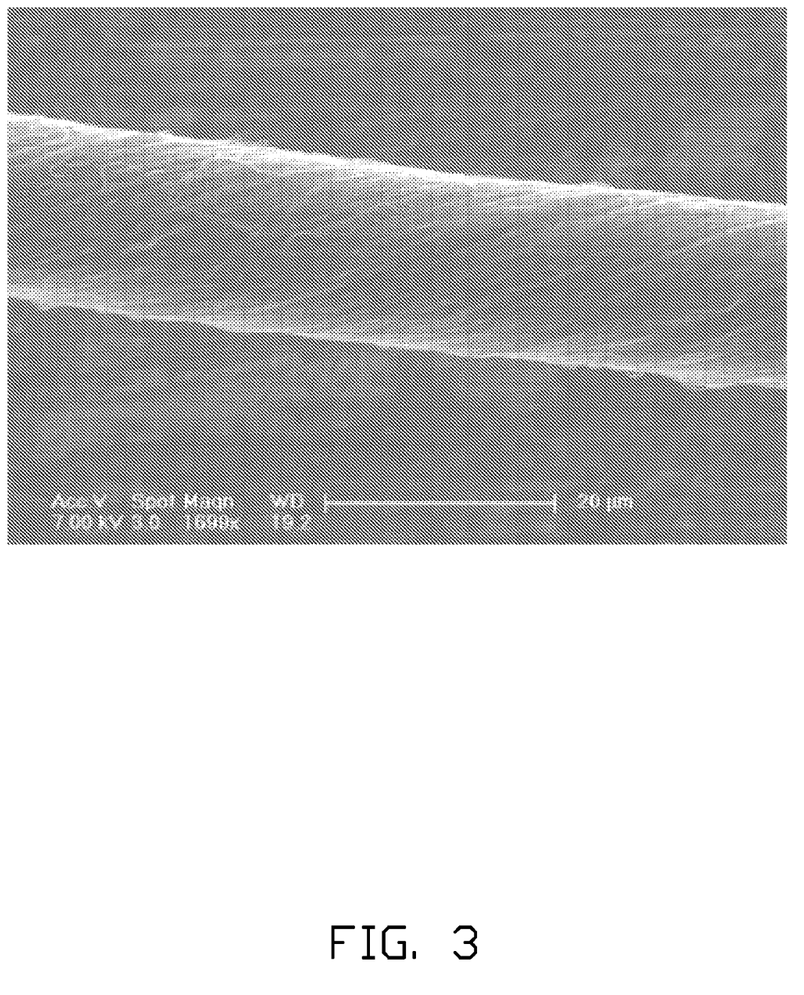
FIG. 3 is a scanning electron microscope (SEM) image of a twisted carbon nanotube wire of a first conductor of the lead in FIG. 2.

The carbon nanotube wire can be a non-twisted carbon nanotube wire or a twisted carbon nanotube wire. Referring to FIG. 3, in one embodiment, the carbon nanotube wire is a twisted carbon nanotube wire. The twisted carbon nanotube wire includes a number of carbon nanotubes oriented around an axis of the twisted carbon nanotube wire. The carbon nanotubes are aligned around the axis of the carbon nanotube twisted wire like a helix. More specifically, the twisted carbon nanotube wire includes a number of successive carbon nanotubes joined end to end by van der Waals attractive force therebetween. Adjacent carbon nanotubes are combined by van der Waals attractive force therebetween to form a number of interspaces. A length and a diameter of the twisted carbon nanotube wire can be set according to practical needs. The twisted carbon nanotube wire can be formed by applying a mechanical force to turn two ends of a drawn carbon nanotube film in opposite directions.

Figure 4:
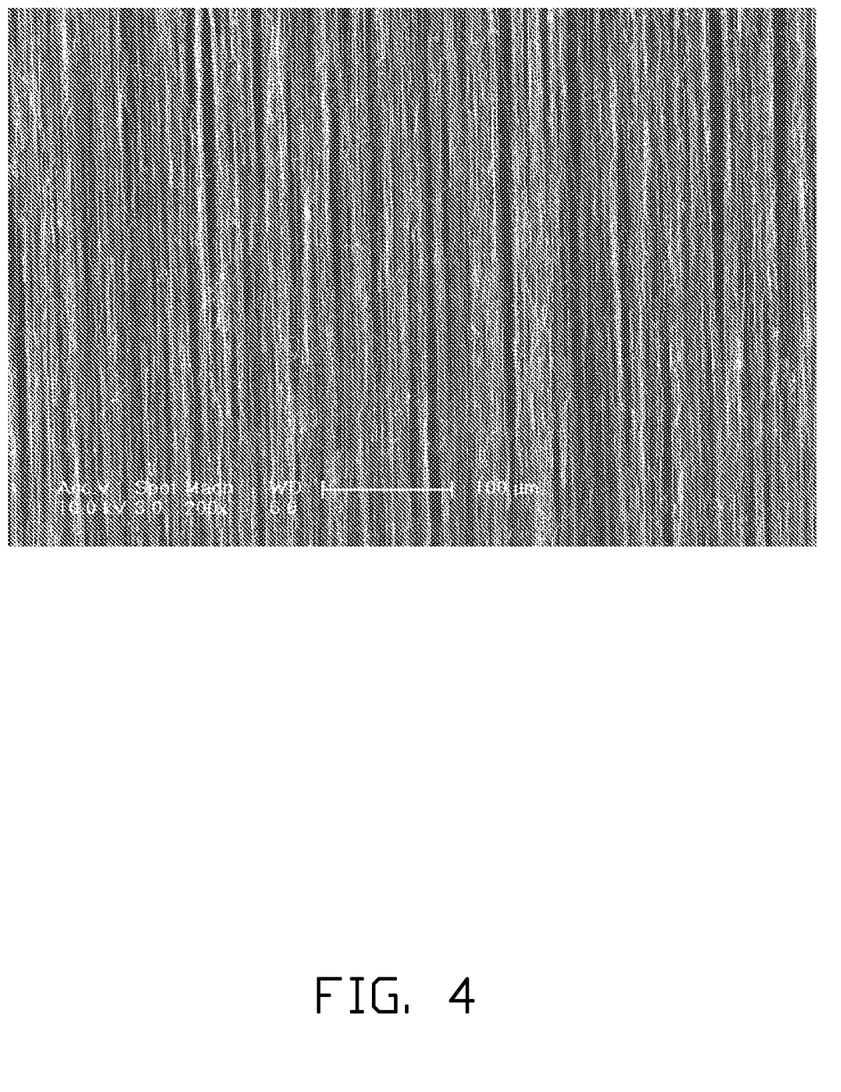
FIG. 4 is an SEM image of a drawn carbon nanotube film for the twisted carbon nanotube wire in FIG. 3.

Referring to FIG. 4, the drawn carbon nanotube film includes a number of carbon nanotubes that are arranged substantially parallel to a surface of the drawn carbon nanotube film. A large number of the carbon nanotubes in the drawn carbon nanotube film can be oriented along a preferred orientation, meaning that a large number of the carbon nanotubes in the drawn carbon nanotube film are arranged substantially along the same direction. An end of one carbon nanotube is joined to another end of an adjacent carbon nanotube arranged substantially along the same direction, by van der Waals force, to form a free-standing film. The term 'free-standing film' includes films that do not have to be supported by a substrate. A small number of the carbon nanotubes are randomly arranged in the drawn carbon nanotube film, and have a small if not negligible effect on the larger number of the carbon nanotubes in the drawn carbon nanotube film arranged substantially along the same direction. It can be appreciated that some variation can occur in the orientation of the carbon nanotubes in the drawn carbon nanotube film. Microscopically, the carbon nanotubes oriented substantially along the same direction may not be perfectly aligned in a straight line, and some curve portions may exist. It can be understood a contact between some carbon nanotubes located substantially side by side and oriented along the same direction cannot be totally excluded. Interspaces are defined in the drawn carbon nanotube film by adjacent carbon nanotubes.

More specifically, the drawn carbon nanotube film can include a number of successively oriented carbon nanotube segments joined end-to-end by van der Waals force therebetween. Each carbon nanotube segment includes a number of carbon nanotubes substantially parallel to each other, and joined by van der Waals force therebetween. The carbon nanotube segments can vary in width, thickness, uniformity and shape. The carbon nanotubes in the drawn carbon nanotube film are also substantially oriented along a preferred orientation. The width of the drawn carbon nanotube film relates to a carbon nanotube array from which the drawn carbon nanotube film is drawn.

Figure 5:
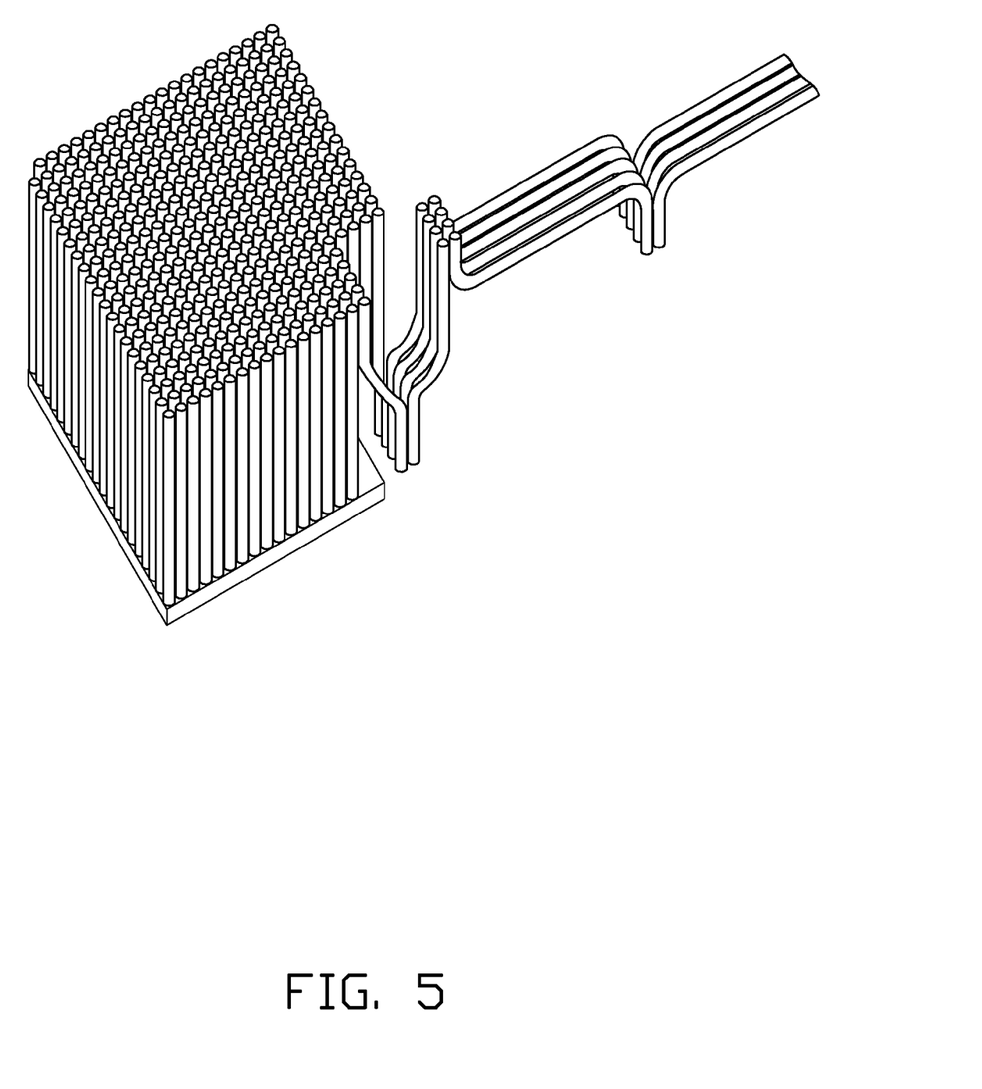
FIG. 5 shows drawing the drawn carbon nanotube film in FIG. 4 from a carbon nanotube array.

Referring to FIG. 5, the drawn carbon nanotube film can be drawn from the carbon nanotube array. The method for drawing the drawn carbon nanotube film includes: providing the carbon nanotube array capable of having a film drawn there from; and pulling/drawing out the drawn carbon nanotube film from the carbon nanotube array. The pulling/drawing can be done by using a tool (e.g., adhesive tape, pliers, tweezers, or another tool allowing multiple carbon nanotubes to be gripped and pulled simultaneously).

The carbon nanotube array can be formed by a chemical vapor deposition method. The carbon nanotube array includes a number of carbon nanotubes parallel to each other and approximately perpendicular to a substrate. The carbon nanotubes in the carbon nanotube array are closely packed together by van der Waals force. The carbon nanotubes in the carbon nanotube array can be single-walled carbon nanotubes, double-walled carbon nanotubes, multi-walled carbon nanotubes, or combinations thereof. Diameters of the carbon nanotubes can be in the range from about 0.5 nanometers to about 50 nanometers. Heights of the carbon nanotubes can be in the range from about 50 nanometers to 5 millimeters. In one embodiment, the height of the carbon nanotubes can be in a range from about 100 microns to 900 microns.

The drawn carbon nanotube film can be pulled/drawn by the following sub-steps: selecting a carbon nanotube segment having a predetermined width from the carbon nanotube array; and pulling the carbon nanotube segment at an even/uniform speed to achieve a uniform drawn carbon nanotube film. More specifically, during the pulling process, as the initial carbon nanotube segment is drawn out, other carbon nanotube segments are also drawn out end-to-end due to the van der Waals force between the ends of the adjacent segments. This process of drawing ensures that a continuous, uniform drawn carbon nanotube film having a predetermined width can be formed.

Figure 6:
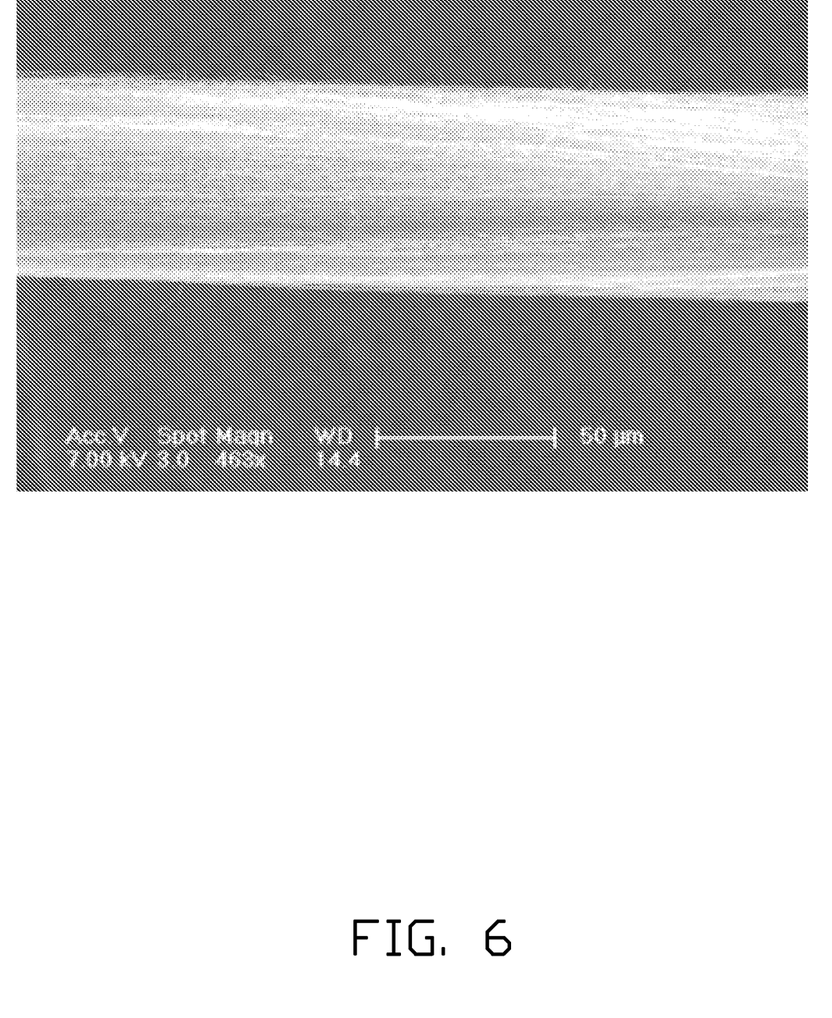
FIG. 6 is an SEM image of a non-twisted carbon nanotube wire of a first conductor of the lead in FIG. 2.

Referring to FIG. 6, the non-twisted carbon nanotube wire includes a number of carbon nanotubes substantially oriented along a same direction (i.e., a direction along the length of the non-twisted carbon nanotube wire). The carbon nanotubes are parallel to the axis of the non-twisted carbon nanotube wire. Specifically, the non-twisted carbon nanotube wire includes a number of successive carbon nanotube segments joined end to end by van der Waals attractive force therebetween. Each carbon nanotube segment includes a number of carbon nanotubes substantially parallel to each other, and combined by van der Waals attractive force therebetween.

The non-twisted carbon nanotube wire can be formed by treating the drawn carbon nanotube film with an organic solvent. Specifically, the drawn carbon nanotube film is treated by applying the organic solvent to the drawn carbon nanotube film to soak an entire surface of the carbon nanotube film. After being soaked by the organic solvent, the adjacent paralleled carbon nanotubes in the drawn carbon nanotube film will bundle together, due to a surface tension of the organic solvent when the organic solvent volatilizing, and thus, the drawn carbon nanotube film will be shrunk into non-twisted carbon nanotube wire. The organic solvent is volatile.

Referring to FIG. 2 again, the insulation layer 244 can be located on an outer surface of the first conductor 242 to form a tube structure. The insulation layer 244 is used to make the first conductor 242 insulate from the outer environment. A material of the insulation layer 244 can be any suitable insulated material, such as polytetrafluoroethylene, polyethylene, polypropylene, polystyrene, polyethylene foam and nano-clay-polymer composite material. In one embodiment, the material of the insulation layer 244 is polyethylene foam.

The shielding layer 246 can be located on an outer surface of the insulation layer 244 and can be used to shield electromagnetic signals or external signals. The shielding layer 246 can be a carbon nanotube structure including a number of radioactive particles located in the carbon nanotube structure. The radioactive particles can be uniformly distributed in the whole structure or different sections of the carbon nanotube structure. In some embodiments, the radioactive particles are uniformly distributed in the sections of the carbon nanotube structure adjacent to the fixing member 26 and the electrode 28. Thus, an excessive fibrotic tissue growth on the fixing member 26 and the electrode 28 can be reduced. In one embodiment, the radioactive particles are uniformly distributed in the whole structure of the carbon nanotube structure. Half-life of the radioactive particles can be less than 100 days. In some embodiments, the half-life of the radioactive particles is less than 10 days. A type of decay of the radioactive particles can be $\beta^-$ decay, which does not travel far in human tissue. A material of the radioactive particles can be $^{32}P$, $^{35}S$, $^{47}Ca$, $^{89}Sr$, $^{111}Ag$, $^{198}Au$, or $^{199}Au$.

In some embodiments, the carbon nanotube structure of the shielding layer 246 having the radioactive particles therein is formed by the steps of: distributing the radioactive particles in a carbon nanotube film or a carbon nanotube wire by a dipping method or a the vacuum evaporating method; and winding the carbon nanotube wire or the carbon nanotube film having the radioactive particles therein around the insulating layer 244. In other embodiments, the carbon nanotube structure having the radioactive particles therein is formed by steps of: winding a carbon nanotube wire or a carbon nanotube film around the insulating layer 244 to form the carbon nanotube structure; and distributing the radioactive particles in the carbon nanotube structure by the dipping method or the vacuum evaporating method. The carbon nanotube films can be drawn carbon nanotube films, pressed carbon nanotube films or flocculated carbon nanotube films. The carbon nanotube wires can be twisted carbon nanotube wires or non-twisted carbon nanotube wires.

Figure 7:
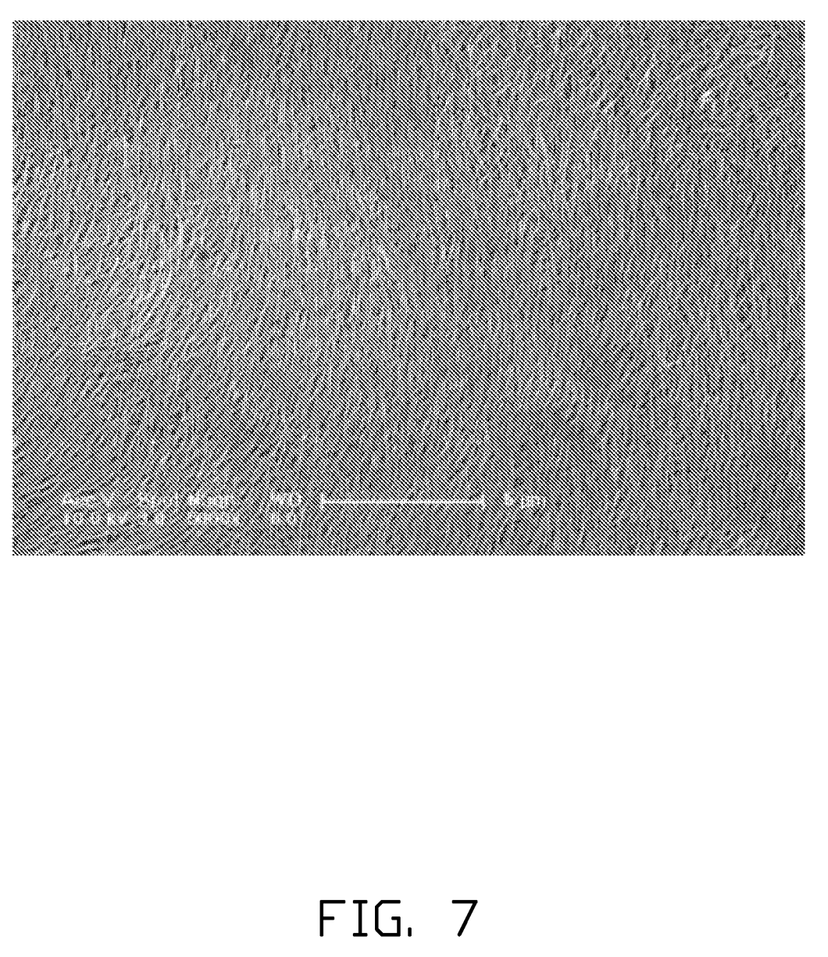
FIG. 7 is an SEM image of a pressed carbon nanotube film of a shielding layer of the lead in FIG. 2.

The pressed carbon nanotube films can be formed by pressing a carbon nanotube array down on a substrate. Referring to FIG. 7, the carbon nanotubes in the pressed carbon nanotube array are arranged along a same direction or along different directions. The carbon nanotubes in the pressed carbon nanotube array can rest upon each other. Adjacent carbon nanotubes are attracted to each other and combined by van der Waals force. An angle between a primary alignment direction of the carbon nanotubes and a surface of the pressed carbon nanotube array is about 0 degrees to about 15 degrees. The greater the pressure applied, the smaller the angle obtained. When the carbon nanotubes in the pressed carbon nanotube array are arranged along different directions, the carbon nanotube structure can be isotropic. The thickness of the pressed carbon nanotube array can range from about 0.5 nanometer to about 1 millimeter. The length of the carbon nanotubes can be larger than 50 micrometers.

Figure 8:
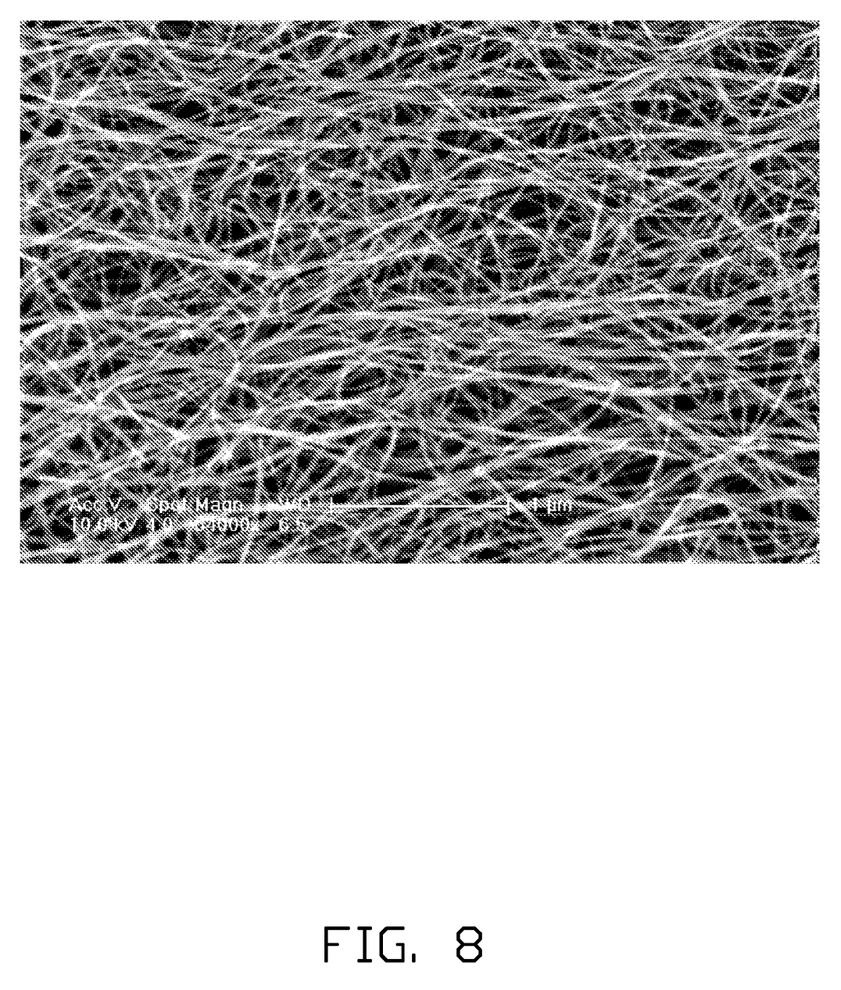
FIG. 8 is an SEM image of a flocculated carbon nanotube film of a shielding layer of the lead in FIG. 2.

The flocculated carbon nanotube film can be formed by a flocculating method. Referring to FIG. 8, the flocculated carbon nanotube film can include a number of long, curved, disordered carbon nanotubes entangled with each other. A length of the carbon nanotubes can be greater than 10 centimeters. Further, the flocculated carbon nanotube film can be isotropic. Here, "isotropic" means the carbon nanotube film has properties identical in all directions substantially parallel to a surface of the carbon nanotube film. The carbon nanotubes can be substantially uniformly distributed in the carbon nanotube film. The adjacent carbon nanotubes are acted upon by the van der Waals force therebetween. A thickness of the flocculated carbon nanotube film can range from about 1 micrometer to about 1 millimeter.

In one embodiment, the carbon nanotube structure of the shielding layer 246 includes at least one flocculated carbon nanotube film, the at least one flocculated carbon nanotube film can be closely and uniformly combined to the outer surface of the insulating layer 244 by van der Waals force to form the shielding layer 246. The at least one flocculated carbon nanotube film can be spirally arranged along the insulating layer 244. The carbon nanotubes of the shielding layer 246 can be substantially entangled with each other and adjacent carbon nanotubes can combined with each other firmly by van der Waals force therebetween.

In another embodiment, the carbon nanotube structure includes at least one drawn carbon nanotube film, or at least one untwisted carbon nanotube wire. The at least one drawn carbon nanotube film or at least one untwisted carbon nanotube wire can be closely and uniformly combined to the outer surface of the insulating layer 244 by van der Waals force to form the carbon nanotube structure. Most of the carbon nanotubes can be arranged around an axis of the insulating layer 244. Most adjacent carbon nanotubes substantially extending along the same direction are joined end-to-end by van der Waals force. Furthermore, most of the carbon nanotubes can substantially spirally extend along the axis of the insulating layer 244. An angle is defined between most of the carbon nanotubes and the axis of the insulating layer 244. The angle can be larger than or equal to 0 degree and less than 90 degrees. Carbon nanotubes in each drawn carbon nanotube film or untwisted carbon nanotube wire can extend along a same direction, such that angles defined between most of the carbon nanotubes and the axis of the insulating layer 244 can be substantially equal to each other. In one embodiment, the angle is equal to about 0 degree. In other words, most of carbon nanotubes in the carbon nanotube structure are arranged along the axis of the insulating layer 244.

In still another embodiment, the carbon nanotube structure includes at least one pressed carbon nanotube film. The at least one pressed carbon nanotube film can be closely and uniformly combined to the outer surface of the insulating layer 244 by van der Waals force to form the carbon nanotube structure. The at least one pressed carbon nanotube film can be substantially spirally coiled around the axis of the insulating layer 244. If the at least one pressed carbon nanotube film includes a number of carbon nanotubes arranged along different directions, the carbon nanotubes can be disorderly, uniformly, and tightly arranged along the outer surface of the insulating layer 244. If the at least one pressed carbon nanotube film includes a number of carbon nanotubes arranged along a same direction. The carbon nanotubes can be uniformly and tightly arranged along the outer surface of the insulating layer 244, and adjacent carbon nanotubes are attracted to each other and combined by van der Waals force. An angle between an arranged direction of the carbon nanotubes and the axis of the insulating layer 244 can be larger than or equal to about 0 degrees and less than 90 degrees.

In one embodiment, the carbon nanotube structure of the shielding layer 246 includes at least one twisted carbon nanotube wire. The at least one twisted carbon nanotube wire can be closely and uniformly combined to the outer surface of the insulating layer 244 by van der Waals force to form the carbon nanotube structure. Most of the carbon nanotubes are joined end-to-end and uniformly located around the axis of the insulating layer 244 by van der Waals force therebetween.

The radioactive particles can be uniformly distributed in the interspaces of the carbon nanotube structure or filled in hollow structures of carbon nanotubes of the carbon nanotube structure to form a composited structure. In one embodiment, the shielding layer 246 is formed by the steps of providing an organic solvent with a number of nano-scale $^{198}$Au particles uniformly distributed therein; immersing a drawn carbon nanotube film into the organic solvent; removing the drawn carbon nanotube film from the organic solvent and drying the drawn carbon nanotube film; and winding the drawn carbon nanotube film having the nano-scale $^{198}$Au particles therein on the outer surface of the insulating layer 244 to form the shielding layer 246. The nano-scale $^{198}$Au particles are located in the interspaces of the carbon nanotube structure and filled in hollow structures of carbon nanotubes of the carbon nanotube structure, thus, the conductive property of the shielding layer 246 can be dramatically increased. A diameter of the nano-scale $^{198}$Au particles is from about 1 nanometer to about 100 nanometer. The nano-scale $^{198}$Au particles also can be filled or composited in joints between two joined end to end carbon nanotubes of the carbon nanotube drawn film, thus the conductivity and shielding performance of the first shielding layer 246 can be remarkably increased even if an amount of the nano-scale the first shielding layer can be remarkably increased even if an amount of the nano-scale $^{198}$Au particles in the carbon nanotube drawn film is relatively low.

The sheath 248 can be located on an outer surface of the shielding layer 246 and can be used to prevent the lead 24 from machinery damage, chemical exposure damage, etc. A material of the sheath 248 can be polymer material having bio-compatibility and corrosion resistance characteristics. The material of the sheath 248 can be polyurethane or silicone rubber. In one embodiment, the material of the sheath 248 is polyurethane.

The fixing member 26 can be fixed on an outer surface of the sheath 248 adjacent to the electrode 28. The fixing member 26 can also be made of polymer material like polyurethane or silicone rubber. The fixing member 26 can include a fixing ring 262 and a number of fixing wings 264. The fixing ring 262 can have a cylindrical structure. The fixing wings 264 can have a claviform structure extending along a direction from an axis of the fixing ring 262 to an outer surface of the fixing ring 262. An angle between the axis of the claviform structure and the axis of the fixing ring 262 can be in the range from about 30 degrees to about 60 degrees. The fixing wing 264 can be wrapped with human tissue after the fixing member 26 is implanted into the human body to fix the electrode 28 in place.

A material of the electrode 28 can be metals or alloys having good conductivity. In one embodiment, the electrode 28 is made of platinum-iridium alloy. The electrode 28 can include a coating layer located on a surface of the electrode 28. A material of the coating layer can be porous materials having bio-compatibility. The material of the coating layer can be activated carbon, carbon fiber, carbon nanotube, platinum-iridium alloy or titanium nitride composite. In one embodiment, the coating layer is activated carbon.

In use of the pacemaker 100, the electrode line 20 is implanted into the body, and the electrode 28 is fixed to contact a chosen tissue by the fixing member 26. The electrical pulse signals can be generated by the control circuit and transported to the electrode 28 by the first conductor 242 to stimulate the chosen tissue and achieve purpose of treating the chosen tissue.

Figure 9:
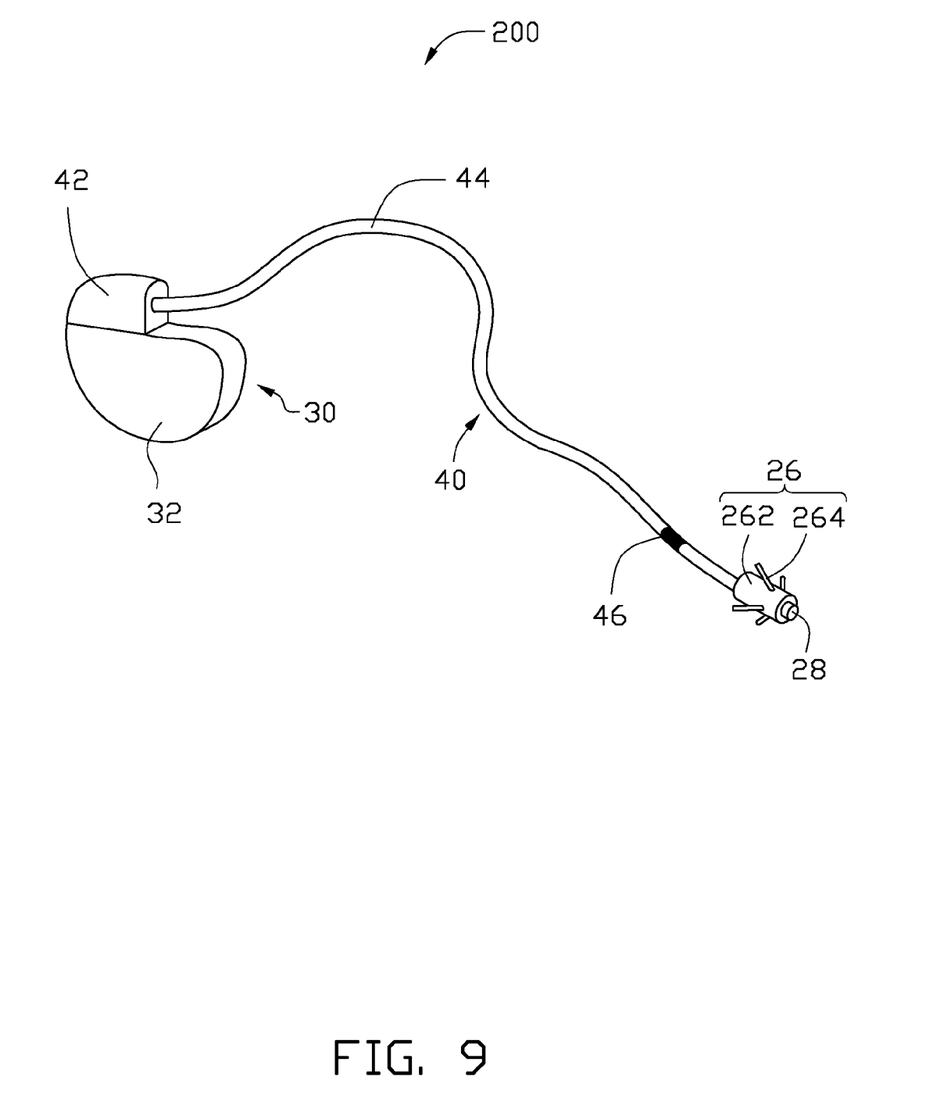
FIG. 9 shows a schematic structural view of another embodiment of a pacemaker.

Referring to FIG. 9, a pacemaker 200 of another embodiment is provided. The pacemaker 100 is a bipolar pacemaker. The pacemaker 100 includes a pulse generator 30 and an electrode line 40 electrically connected to the pulse generator 30. The pulse generator 30 can generate electrical pulse signals traveling through the electrode line 40 to stimulate the brain heart tissue or the heart tissue. The pulse generator 30 includes a shell 32, a power source (not shown), a control circuit (not shown) and a sense circuit (not shown). The power source, the control circuit and sense circuit are electrically connected to each other.

The electrode line 40 includes an interface 42, a lead 44, a ring electrode 46, the fixing member 26 and the electrode 28.

The interface 42 includes a first conductive contact (not shown) and second conductive contact (not shown). The first conductive contact is electrically connected to the control circuit. The second conductive contact is electrically connected to the sense circuit.

Figure 10:
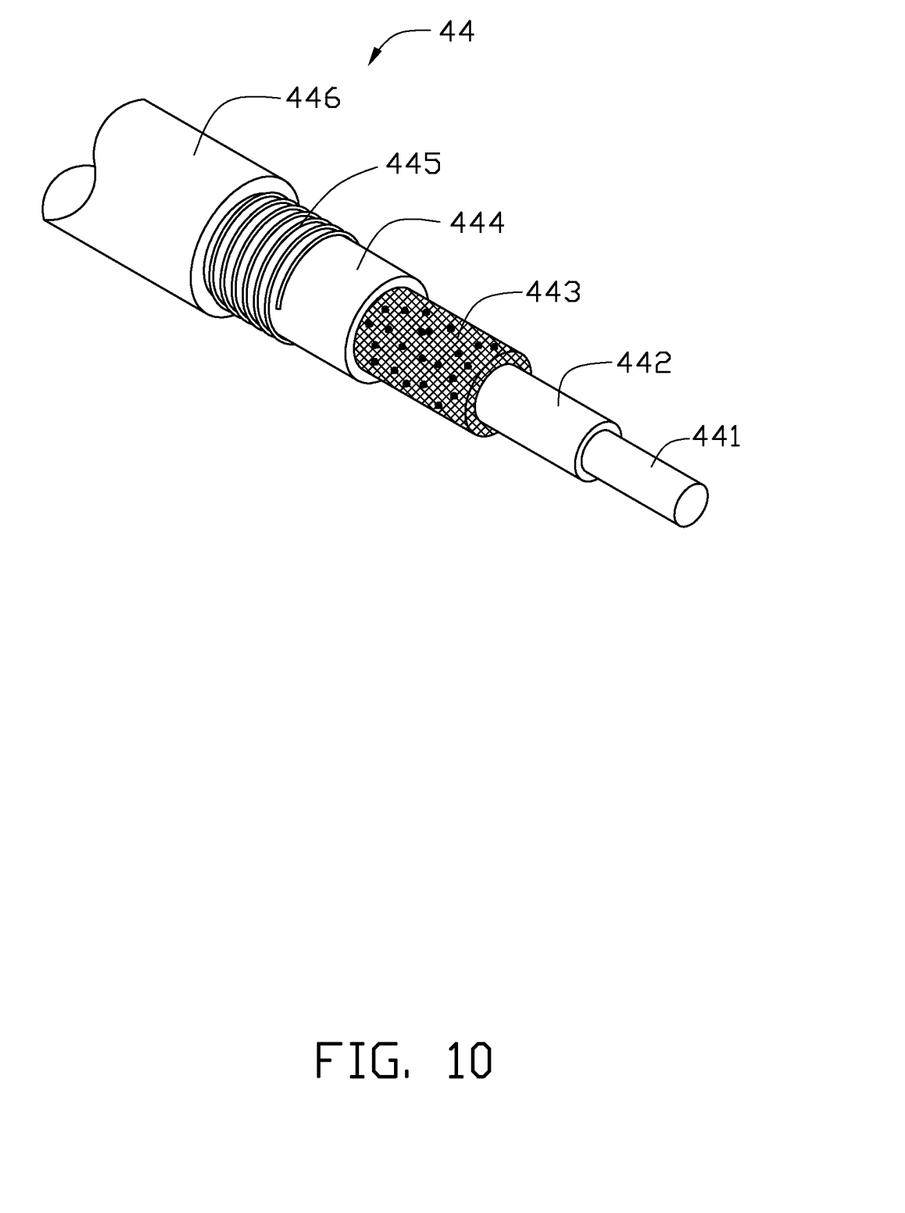
FIG. 10 shows a schematic structural view of a lead of the pacemaker in FIG. 9.

Referring to FIG. 10, the lead 44 includes a first conductor 441, an first insulation layer 442, a shielding layer 443, a second insulation layer 444, a second conductor 445 and a sheath 446 arranged from inside to outside.

The first conductor 441 is the same as the first conductor 242. The first conductor 441 can also be a twisted carbon nanotube wire or a non-twisted carbon nanotube wire having a number of radioactive particles therein. A first end of the first conductor 441 is electrically connected to the first conductive contact, a second end of the first conductor 441 is electrically connected to the electrode 28. Thus, the electrode 28 can be electrically connected to control circuit through the first conductor 441 and the first conductive contact.

The first insulation layer 442 can be located on an outer surface of the first conductor 441. A material of the first insulation layer 442 can be polytetrafluoroethylene, polyethylene, polypropylene, polystyrene, polyethylene foam, and nano-clay-polymer composite material. In one embodiment, the insulation layer 442 is polyethylene foam.

The shielding layer 443 can be located on an outer surface of the first insulation layer 442 and can be used to shield electromagnetic signals or external signals. In one embodiment, the insulation layer is made of a drawn carbon nanotube film having a number of radioactive particles therein.

The second insulation layer 444 can be located on an outer surface of the shielding layer 443. A material of the second insulation layer 444 can be polytetrafluoroethylene, polyethylene, polypropylene, polystyrene, polyethylene foam and nano-clay-polymer composite material.

The second conductor 445 is located on an outer surface of the second insulation layer 444. The second conductor 445 can be a carbon nanotube wire. The carbon nanotube wire can wind along an axis of the second insulation layer 444 or substantially parallel to the axis of the second insulation layer 444. The carbon nanotube wire can include a number of radioactive particles therein. In one embodiment, the second conductor 445 is a twisted carbon nanotube wire winding along the axis of the second insulation layer 444. A first end of the second conductor 445 is electrically connected the second conductive contact, a second end of the second conductor 445 is electrically connected the ring electrode 46. Thus, the ring electrode 46 can be electrically connected to the sense circuit through the second conductor 445 and the second conductive contact.

The sheath 446 can be located on an outer surface of the second conductor 445 and can be used to prevent the lead 44 from machinery damage, chemical exposure damage, etc.

The ring electrode 46 can be located on an outer surface of sheath 446 adjacent to the electrode 28. The ring electrode 46 can be a conductive coil and is electrically connected to the second conductor 445. A material of the ring electrode 46 can be metals or alloys having good conductivity. In one embodiment, the electrode 28 is made of platinum-iridium alloy.

In some embodiments, the second conductor 445 is located on the outer surface of first insulation layer 442, and the shielding layer 443 is located on the outer surface of second insulation layer 444. Thus, the shielding layer 443 can be used to shield the first insulation layer 442 and the second conductor 445 from external electromagnetic signals or external signals.

In use of the pacemaker 200, the electrode line 40 is implanted into the tissue of body, and the electrode 28 is fixed to contact a chosen tissue by the fixing member 26. A sensing signal can be obtained from the chosen tissue by the ring electrode 46 and transported to the sense circuit and the control circuit by the second conductor 445. Then, an electrical pulse signal can be generated by the control circuit according the sensing signal and transported to electrode 28 by the first conductor 441. The electrical pulse signal can stimulate the chosen tissue and achieve the purpose of treating the chosen tissue.

The pacemaker has the following advantages. When the electrode line with the radioactive particles is implanted into the tissue of the body, the radioactive particles can prevent an excessive fibrotic tissue growth on the electrode line. Thus, the electrode line of the pacemaker can be easily removed from the tissue after therapy. The radioactive particles is distributed in the interspaces of the carbon nanotube structure or filled in the hollow structure of carbon nanotubes of the carbon nanotube structure to form the shielding layer. Thus, the conductivity of the electrode line can be increased. The carbon nanotube wires or the carbon nanotube films are closely and uniformly combined to an outer surface of the insulating layer by van der Waals force to from the shielding layer. Thus, the toughness and mechanical strength of the electrode line can be increased. The conductor of the electrode line is composed of carbon nanotubes, thus, the conductor has a good conductivity. The efficiency of the pacemaker can be improved.

It is to be understood, however, that even though numerous characteristics and advantages of certain inventive embodiments have been set out in the foregoing description, together with details of the structures and functions of the embodiments, the disclosure is illustrative only; and that changes may be made in detail, especially in matters of arrangement of parts within the principles of the present disclosure to the full extent indicated by the broad general meaning of the terms in which the appended claims are expressed.

What is claimed is:

1. An electrode line comprising at least one lead, the at least one lead comprising:
a first conductor;
a first insulation layer located on an outer surface of the first conductor; and
a shielding layer locating on an outer surface of the first insulation layer;
wherein the shielding layer is a carbon nanotube structure comprising a plurality of radioactive particles therein; the carbon nanotube structure comprises a plurality of carbon nanotubes joined end to end by van der Waals force along an extending direction of the carbon nanotube structure, the carbon nanotube structure has a plurality of joints, each of the plurality joints are formed between two carbon nanotubes which are joined end to end, and the plurality of radioactive particles are filled in the plurality of joints.

2. The electrode line of claim 1, wherein the plurality of radioactive particles is uniformly distributed in different sections of the carbon nanotube structure.

3. The electrode line of claim 1, wherein a half-life of the plurality of radioactive particles is less than 100 days.

4. The electrode line of claim 3, wherein the half-life of the plurality of radioactive particles is less than 10 days.

5. The electrode line of claim 1, wherein a material of the plurality of radioactive particles is selected from the group consisting of $^{32}P$, $^{35}S$, $^{47}Ca$, $^{89}Sr$, $^{111}Ag$, $^{115}Cd$, $^{185}W$, $^{198}Au$, and $^{199}Au$.

6. The electrode line of claim 1, wherein a decay type of the plurality of radioactive particles is $\beta^-$ decay.

7. The electrode line of claim 1, wherein the adjacent carbon nanotubes are combined firmly by van der Waals force to form a plurality of interspaces.

8. The electrode line of claim 7, wherein the plurality of carbon nanotubes are oriented around an axis of the first conductor.

9. The electrode line of claim 7, wherein the plurality of carbon nanotubes are parallel to an axis of the first conductor.

10. A pacemaker, comprising:
a pulse generator; and
an electrode line connecting with the pulse generator, the electrode line comprising at least one conductor comprising:
a first conductor;
a first insulation layer located on an outer surface of the first conductor; and
a shielding layer located on an outer surface of the first insulation layer;
wherein the shielding layer has a carbon nanotube structure comprising a plurality of radioactive particles; the carbon nanotube structure comprises a plurality of carbon nanotubes, a diameter of each of the plurality of radioactive particles is from about 1 nm to about 100 nm, the carbon nanotube structure has a plurality of joints, each of the plurality joints are formed between two carbon nanotubes which are joined end to end, and the plurality of radioactive particles are filled in the plurality of joints.

11. The pacemaker of claim 10, wherein the carbon nanotube structure comprises at least one carbon nanotube film or at least one carbon nanotube wire closely and uniformly combined to the outer surface of the first insulation layer by van der Waals force.

12. The pacemaker of claim 11, wherein the at least one carbon nanotube wire or the at least one carbon nanotube film is spirally arranged along the outer surface of the first insulating layer.

13. The pacemaker of claim 11, wherein the plurality of radioactive particles is uniformly distributed in the at least one carbon nanotube film or the at least one carbon nanotube wire.

14. An electrode line comprising at least one lead, the at least one lead comprising;
a first conductor;
a first insulation layer disposed on an outer surface of the first conductor;
a shielding layer disposed on an outer surface of the first insulation layer, the shielding layer being a carbon nanotube structure comprising a plurality of first radioactive particles therein, wherein the carbon nanotube wire is a twisted carbon nanotube wire comprising a plurality of second radioactive particles therein, the carbon nanotube structure has a plurality of joints, each of the plurality joints are formed between two carbon nanotubes which are joined end to end, and the plurality of radioactive particles are filled in the plurality of joints;
a second insulation layer disposed on an outer surface of the shielding layer; and a second conductor disposed on an outer surface of the second insulation layer, wherein the second conductor is a carbon nanotube wire wound along an axis of the second insulation layer, the carbon nanotube wire comprises a plurality of carbon nanotubes joined end to end by van der Waals force along an extending direction of the carbon nanotube wire.

15. The electrode line of claim 14 further comprising a sheath disposed on an outer surface of the second conductor.

* * * * *